United States Patent [19]

Shum et al.

[11] Patent Number: 5,118,822

[45] Date of Patent: Jun. 2, 1992

[54] OLEFIN EPOXIDATION USING A PERRHENATE CATALYST AND AN ORGANIC HYDROPEROXIDE

[75] Inventors: Wilfred P. Shum, West Chester; Haven S. Kesling, Jr., Drexel Hill, both of Pa.

[73] Assignee: Arco Chemical Technology, L.P., Wilmington, Del.

[21] Appl. No.: 767,594

[22] Filed: Sep. 30, 1991

[51] Int. Cl.$^5$ .................................. C07D 301/19
[52] U.S. Cl. ................... 549/529; 569/909.8
[58] Field of Search .......................... 549/529

[56] References Cited

U.S. PATENT DOCUMENTS

| | | | |
|---|---|---|---|
| 3,316,279 | 4/1967 | Fenton | 260/348.5 |
| 3,351,635 | 11/1967 | Kollar | 260/348.5 |
| 3,360,585 | 12/1967 | Winnick | 549/529 |
| 3,391,214 | 7/1968 | Fetterly | 549/529 |
| 3,475,498 | 10/1969 | Choo | 549/529 |
| 3,489,775 | 1/1970 | de Roch et al. | 549/529 |
| 3,518,285 | 6/1970 | Fenton et al. | 260/348.5 |
| 3,536,732 | 10/1970 | Borchert et al. | 549/529 |
| 3,745,178 | 7/1973 | White | 549/529 |
| 3,778,451 | 12/1973 | Poite | 260/348.5 |
| 3,849,451 | 11/1974 | Stein et al. | 549/529 |
| 3,860,662 | 1/1975 | Kollar | 549/529 |
| 3,931,249 | 1/1976 | Stoutzenberger | 549/529 |
| 4,024,165 | 5/1977 | Shryne et al. | 260/348.5 |
| 4,418,203 | 11/1983 | Kim | 549/531 |
| 4,564,715 | 1/1986 | Briggs et al. | 568/867 |
| 4,667,045 | 5/1987 | Briggs et al. | 556/20 |
| 4,822,899 | 4/1989 | Groves et al. | 549/533 |
| 4,864,041 | 9/1989 | Hill | 549/529 |
| 4,982,021 | 1/1991 | Best et al. | 568/867 |
| 4,987,226 | 1/1991 | Buchler et al. | 540/145 |

FOREIGN PATENT DOCUMENTS

| | | |
|---|---|---|
| 308101 | 3/1989 | European Pat. Off. . |
| 308791 | 3/1989 | European Pat. Off. . |
| 3902357 | 8/1990 | Fed. Rep. of Germany . |
| 7513859 | 4/1976 | Netherlands ........................ 549/529 |

OTHER PUBLICATIONS

Kollar, *Preprints, Div. Pet. Chem.* 106 (1978).
Ly et al., *Chem. Ing. Tecfn.* 61(8), 646 (1989).
Jorgensen, *Chem. Rev.* 89(3), 431 (1989).
Herrmann, *J. Organomet. Chem.* 382, 1 (1990).
Sheldon, *J. Mol. Cat.* 7, 107 (1980).
Rummel et al., *Oxid. Commun.* 6, 319 (1984).

*Primary Examiner*—J. E. Evans
*Attorney, Agent, or Firm*—Stephen D. Harper

[57] ABSTRACT

Olefins are oxidized to epoxide compounds by contacting the olefins with organic hydroperoxides in the presence of rhenium catalysts comprised of perrhenate anions and organopnicogen-containing cations. High yields of epoxides are attained, particularly when the olefin substrate bears an aromatic substituent.

29 Claims, No Drawings

OLEFIN EPOXIDATION USING A PERRHENATE CATALYST AND AN ORGANIC HYDROPEROXIDE

FIELD OF THE INVENTION

This invention relates to methods wherein an olefin may be oxidized to an epoxide. More particularly, this invention pertains to catalytic epoxidation processes employing organopnicogen-containing perrhenate compounds as catalysts and organic hydroperoxides as oxidizing agents.

BACKGROUND OF THE INVENTION

Epoxides such as ethylene oxide, propylene oxide, 1,2-butene oxide and the like are useful intermediates for the preparation of a wide variety of products. The oxirane functionality in such compounds is highly reactive and may be ring-opened with any number of nucleophilic reactants. For example, epoxides may be hydrolyzed to yield glycols useful as anti-freeze components, food additives, or reactive monomers for the preparation of condensation polymers such as polyesters.

Polyether polyols generated by the ring-opening polymerization of epoxides are widely utilized as intermediates in the preparation of polyurethane foams, elastomers, sealants, coatings, and the like. The reaction of epoxides with alcohols provides glycol ethers, which may be used as polar solvents in a number of applications.

Many different methods for the preparation of epoxides have been developed. One such method involves the epoxidation of an olefin in a liquid phase reaction using an organic hydroperoxide as the oxidizing agent and certain transition metal compounds as catalyst. Generally speaking, Group IVB, VB, and VIB transition metal compounds have been found to have the highest activity and selectivity in olefin epoxidation reactions using organic hydroperoxides. Metals having low oxidation potentials and high Lewis acidity in their highest oxidation states are superior epoxidation catalysts, according to Sheldon, *J. Mol. Cat.* 7, 107(1980). Molybdenum, tungsten, titanium, and vanadium compounds thus have generally been found to be the most useful catalysts for the reaction of an organic hydroperoxide with an olefin.

Sheldon found that rhenium heptoxide, in contrast to other transition metal compounds, caused rapid, nonproductive decomposition of the hydroperoxide. Thus, an attempt to epoxidize 1-octene with t-butyl hydroperoxide using rhenium heptoxide gave complete conversion of the hydroperoxide to the corresponding alcohol but none of the desired epoxide product. Kollar [U.S. Pat. No. 3,351,635 (Table I); *Preprints, Dev. Pet. Chem.* 106(1978)] also reported extremely low yields of epoxide when the use of a rhenium catalyst in an epoxidation reaction was attempted, apparently due to the very rapid decomposition of the hydroperoxide catalyzed by the rhenium compound. Low selectivity to epoxide was similarly observed using rhenium decacarbonyl as catalyst, cyclohexene as the olefin substrate, and t-butyl hydroperoxide as the oxidant [Rummel et al. *Oxid. Commun.* 6, 319(1984)]. Jorgensen, in a recent review of transition metal catalyzed epoxidations [*Chem. Rev.* 89, 431(1989)], concludes that rhenium complexes are poor epoxidation catalysts using t-butyl hydroperoxide as oxidant. DE 3,902,357 similarly teaches that rhenium oxides are either inactive or nonselective in the oxidation of olefins in the presence of oxidizing agents such as t-butyl hydroperoxide.

To date, rhenium compounds such as rhenium heptoxide have thus been primarily used to promote decomposition reactions of hydroperoxides rather than as oxidation catalysts. For example, the process described in European Pat. Appl. No. 308,101 employs rhenium compounds to catalyze the decomposition of t-butyl hydroperoxide to t-butyl alcohol. Jpn. Kokai No. 63-277,640 (*Chem. Abst.* 110:172753d) teaches cyclohexyl hydroperoxide decomposition to cyclohexanol or cyclohexanone using rhenium heptoxide. U.S. Pat. No. 4,297,518 describes the use of rhenium heptoxide to catalyze the rearrangement of cumene hydroperoxide to phenol and acetone.

It is thus apparent that rhenium compounds have heretofore been found to be of little utility as catalysts for the epoxidation of olefins using alkyl hydroperoxides as the source of oxygen, owing to the tendency of such compounds to favor hydroperoxide decomposition over olefin epoxidation. We have now found that certain perrhenate compounds, in contrast to the rhenium compounds employed in the prior art, are excellent olefin epoxidation catalysts and permit the preparation of epoxides with high selectivity and minimal unproductive hydroperoxide decomposition. The ability of organopnicogen-containing perrhenate compounds to effectively catalyze epoxidation reactions was completely unexpected in view of their ineffectiveness when hydrogen peroxide is employed as the oxidant, as taught in German Pat. No. 3,902,357.

The perrhenate catalysts of this invention are particularly suitable for use in biphasic reaction media containing water and thus can be employed in epoxidations wherein an aqueous organic hydroperoxide solution is the source of the required oxidant. The high selectivity to epoxide realizable in such systems was especially surprising in view of the fact that organopnicogen-containing perrhenate compounds have previously been used to catalyze the hydrolysis of epoxides to glycols as disclosed, for example, in U.S. Pat. No. 4,564,715.

SUMMARY OF THE INVENTION

This invention provides a process for epoxidizing an olefin comprising contacting the olefin with an organic hydroperoxide in the presence of a rhenium catalyst comprised of a perrhenate anion and an organopnicogen-containing cation effective to form an epoxide of the olefin.

In one particular embodiment, the invention provides a process for epoxidizing an olefin wherein at least one of the ethylenically unsaturated functional groups of the olefin bears an aromatic substituent. The process comprises contacting a secondary or tertiary hydroperoxide having the general structure

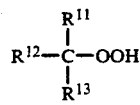

wherein $R^{11}$, $R^{12}$, and $R^3$ are the same or different and are selected from the group consisting of hydrogen, methyl, ethyl, and phenyl in the presence of a rhenium catalyst having the general formula $$[RR^1R^2R^3Pn][ReO_4]$$

wherein R, $R^1$, $R^2$, and $R^3$ are the same or different and are selected from the group consisting of hydrogen, $C_1$-$C_{20}$ linear, branched, or cyclic alkyl, $C_6$-$C_{20}$ aryl, and $C_7$-$C_{20}$ aralkyl, with the proviso that not all of R, $R^1$, $R^2$, and $R^3$ are hydrogen, and Pn is N, P, or As, effective to form an epoxide of the olefin.

In another embodiment, a process for epoxidizing an olefin is provided which comprises contacting the olefin with an organic hydroperoxide in the presence of catalytically effective amounts of an alkali metal perrhenate and an organopnicogen halide salt. Optionally, this process is carried out in the presence of water and a water-immiscible organic solvent such that a biphasic reaction mixture is formed.

DETAILED DESCRIPTION OF THE INVENTION

The catalyst employed in the process of this invention is an organopnicogen-containing perrhenate. Such compounds are well-known and are characterized by having at least one perrhenate anion ($ReO_4^-$) and at least one organopnicogen-containing cation. The cation is comprised of at least one pnicogen, that is, an element of Group VA of the periodic table and at least one organic substituent bonded to or associated with the pnicogen. "Organic substituent" in this context refers to radicals containing, at a minimum, carbon and hydrogen. Preferably, the pnicogen is bonded to or associated with a carbon atom of the organic substituent. The pnicogen is most preferably either nitrogen, phosphorus, or arsenic, but can also be antimony or bismuth. The cation may contain more than one type of pnicogen (e.g., one nitrogen and one phosphorus, one phosphorus and one arsenic). While either one, two, three, or four organic substituents may be bonded to or associated with each pnicogen in the cation, it is preferred that the cation be quaternary in structure with four such substituents being associated with the pnicogen. Without wishing to be bound by theory, it is believed that the organopnicogen-containing cation helps to solubilize the perrhenate anion in the organic-based reaction mixture containing olefin, organic hydroperoxide, and, optionally, organic solvent. Thus, in one embodiment of the process, the reaction mixture is homogeneous. This solubilization is thought to be partially responsible for the favorable catalytic activity of the perrhenate compounds used herein, as alkali metal perrhenates are generally insoluble in such mixtures. Preferably, the organopnicogen-containing cation is selected such that the resulting perrhenate catalyst has a solubility in the reaction mixture at the operable reaction temperature of at least about 1000 ppm. However, the ability of rhenium species to function as effective epoxidation catalysts is not related solely to their solubility in organic media since rhenium heptoxide has appreciable solubility in typical organic solvents and yet is a very poor catalyst for olefin epoxidation using organic hydroperoxide as oxidant.

Suitable organopnicogen-containing cations may have the general formula $$RR^1R^2R^3Pn$$

wherein R, $R^1$, $R^2$, and $R^3$ are the same or different and are selected from the group consisting of hydrogen, $C_1$-$C_{20}$ linear, branched, or cyclic alkyl, $C_6$-$C_{20}$ aryl, and $C_7$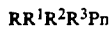$C_{20}$ aralkyl, with the proviso that not all of R, $R^1$, $R^2$, and $R^3$ are hydrogen, and Pn is nitrogen, phosphorus, or arsenic. Examples of $C_1$-$C_{20}$ linear, branched, or cyclic alkyl substituents include, but are not limited to, methyl, ethyl, propyl, butyl (n-,sec-,iso-, tert-), pentyl (and $C_5H_{11}$ isomers), isopropyl, hexyl (and $C_6H_{13}$ isomers), heptyl (and $C_7H_{11}$ isomers), octyl (and $C_{10}H_{17}$ isomers), nonyl (and $C_9H_{19}$ isomers), decyl (and $C_{10}H_{21}$ isomers), undecyl (and $C_{11}H_{23}$ isomers), dodecyl (and $C_{12}H_{25}$ isomers), tridecyl (and $C_{13}H_{27}$ isomers), tetradecyl (and $C_{14}H_{29}$ isomers), pentadecyl (and $C_{15}H_{31}$ isomers), hexadecyl (and $C_{16}H_{33}$ isomers), heptadecyl (and $C_{17}H_{35}$ isomers), octadecyl (and $C_{18}H_{37}$ isomers), nonadecyl (and $C_{19}H_{39}$ isomers), eicosyl (and $C_{20}H_{39}$ isomers), cyclopentyl, cyclohexyl, cyclooctyl, and the like. Examples of $C_6$-$C_{20}$ aryl substituents include phenyl, naphthyl, tolyl, xylyl, mesityl, anthryl, cumenyl, and the like. Suitable $C_7$-$C_{20}$ aralkyl substituents include benzyl, phenethyl, naphthylethyl and the like. The organic substituents may contain, in addition to carbon and hydrogen, other elements such as oxygen, nitrogen, halide (e.g., bromide, chloride), or sulfur in various functional groups such as ester, sulfide, hydroxyl, amine, cyano, nitro, ether, ketone, and the like provided these other elements or functional groups do not detrimentally interfere with the catalytic activity of the organopnicogen-containing perrhenate compound. The R groups may be bonded to each other; thus, the organic substituents attached to the pnicogen may be trimethylene, tetramethylene, pentamethylene, hexamethylene, heptamethylene, cyclohexylene, or other such groups having the general structure $-(R)-$ wherein $-(R)-$ replaces two of the R groups in the formulae given above as well as substituted derivatives thereof. The organic substituents may also comprise an aromatic ring. Thus, suitable organopnicogen-containing cations include pyridinium, bipyridinium, acridinium, and the like and substituted derivatives thereof.

Alternatively, the organopnicogen-containing cation has the general formula

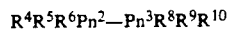

$$R^4R^5R^6Pn^2-Pn^3R^8R^9R^{10}$$

wherein $R^4$, $R^5$, $R^6$, $R^7$, $R^8$, $R^9$, and $R^{10}$ are the same or different and are selected from the group consisting of hydrogen, $C_1$-$C_{20}$ linear, branched, or cyclic alkyl, $C_6$-$C_{20}$ aryl, and $C_7$-$C_{20}$ aralkyl, with the proviso that $R^7$ is not hydrogen, and $Pn^2$ and $Pn^3$ are the same or different and are N, P, or As. The R substituents may be any of the types taught hereinabove in reference to the monopnicogen-containing embodiment of the invention. The $R^7$ substituent linking the two pnicogens may, for example, be any substituent in the series $(CH_2)_n$ wherein n is an integer of from 1 to 20 or any substituted derivative or branched or cyclic isomer thereof as well as a substituent such as phenylene, cyclohexylene, phenylmethylene, phenyldimethyl, and the like.

The organic substituents in the cation component of this invention may, particularly where the pnicogen is other than nitrogen, alternatively be selected such that R is a heteroatom-containing organic group wherein the heteroatom is bonded to or associated with the pnicogen. In this embodiment, the heteroatom may be oxygen, nitrogen, or the like. For example, alkoxy, phenoxy, aralkyoxy, or amino groups can be employed as an organic substituent.

Specific illustrative examples of organopnicogen-containing cations suitable for use in the process of this invention include, but are not limited to, tetrahydrocarbyl ammoniums such as tetramethyl ammonium, tetraethyl ammonium, tetra-n-propyl ammonium, tetra-n-butyl ammonium, tetra-isobutyl ammonium, trimethyl butyl ammonium, tetraheptyl ammonium, tetraphenyl ammonium, tetrabenzyl ammonium, tetradodecyl ammonium, tetraoctadecyl ammonium, 1-ethylpyridinium, 1-ethylquinolinium, 1-ethylquinaldinium, 1-hexadecylpyridinium, hexadecyltrimethyl ammonium, methyl triphenyl phosphonium, 1-[(m-nitrobenzyloxy)methyl]-pyridinium, nonyltrimethyl ammonium, 1-phenethyl-2-picolinium, tetrakis(2-hydroxyethyl)ammonium, tricaprylmethyl ammonium, triethylphenyl ammonium, trioctyl propyl ammonium, benzyldimethyl hexadecyl ammonium, benzyldimethyl phenyl ammonium, benzyltriethyl ammonium, benzyltrimethyl ammonium, bis(2-hydroxyethyl)dimethyl ammonium, (2-chloroethyl)-trimethyl ammonium, decyltrimethyl ammonium, didodecyldimethyl ammonium, dimethyl di-octadecyl ammonium, dodecyl trimethyl ammonium, ethyl hexadecyl dimethyl ammonium, and the like; trihydrocarbyl ammoniums, e.g., trimethyl ammonium, triethyl ammonium, triphenyl ammonium, tridodecyl ammonium, trioctadecyl ammonium, and the like; dihydrocarbyl ammoniums, e.g., dimethyl ammonium, diethyl ammonium, di-n-butyl ammonium, di-n-heptyl ammonium, diphenyl ammonium, dibenzyl ammonium, didodecyl ammonium, dioctadecyl ammonium, and the like; hydrocarbyl ammoniums, e.g., methyl ammonium, n-butyl ammonium, dodecyl ammonium, octadecyl ammonium, phenyl ammonium, benzyl ammonium, and the like; tetrahydrocarbyl phosphoniums, e.g., tetramethyl phosphonium, tetraethyl phosphonium, tetra-n-propyl phosphonium, tetra-n-butyl phosphonium, tetra-isobutyl phosphonium, trimethyl butyl phosphonium, tetraheptyl phosphonium, tetraphenyl phosphonium, tetrabenzyl phosphonium, tetradodecyl phosphonium, tetraoctadecyl phosphonium, chloromethyl triphenyl phosphonium, methoxymethyl triphenyl phosphonium, 2-chloroethyl triphenyl phosphonium, cyclopropyl methyl triphenyl phosphonium, 3-phenylpropyl triphenyl phosphonium, 2-butyl triphenyl phosphonium, cyclohexyl triphenyl phosphonium, n-hexadecyl triphenyl phosphonium, isoamyl triphenyl phosphonium, benzyl triphenyl phosphonium, 4-n-butoxybenzyl triphenyl phosphonium, 4-fluorobenzyl triphenyl phosphonium, 2-nitrobenzyl triphenyl phosphonium, 1-naphthylmethyl triphenyl phosphonium, triphenyl methyl triphenyl phosphonium, and the like; trihydrocarbyl phosphoniums, e.g., trimethyl phosphonium, triethyl phosphonium, triphenyl phosphonium, tridodecyl phosphonium, trioctadecyl phosphonium, and the like; dihydrocarbyl phosphoniums, e.g., dimethyl phosphonium, diethyl phosphonium, di-n-butyl phosphonium, di-n-heptyl phosphonium, diphenyl phosphonium, dibenzyl phosphonium, didodecyl phosphonium, dioctadecyl phosphonium, and the like; hydrocarbyl phosphoniums, e.g., methyl phosphonium, n-butyl phosphonium, octadecyl phosphonium, phenyl phosphonium, benzyl phosphonium, and the like.

Also suitable are tetrahydrocarbyl arsoniums such as tetrahydrocarbyl arsoniums e.g., tetramethyl arsonium, tetraethyl arsonium, tetra-n-propyl arsonium, tetra-n-butyl arsonium, tetra-isobutyl arsonium, trimethyl butyl arsonium, tetraheptyl arsonium, tetraphenyl arsonium, tetrabenzyl arsonium, tetradodecyl arsonium, tetraoctadecyl arsonium, and the like; trihydrocarbyl arsoniums, e.g., trimethyl arsonium, triethyl arsonium, triphenyl arsonium, tridodecyl arsonium, trioctadecyl arsonium, and the like; dihydrocarbyl arsoniums, e.g., dimethyl arsonium, diethyl arsonium, di-n-butyl arsonium, di-n-heptyl arsonium, diphenyl arsonium, dibenzyl arsonium, didodecyl arsonium, dioctadecyl arsonium, and the like; hydrocarbyl arsoniums, e.g., methyl arsonium, n-butyl arsonium, dodecyl arsonium, octadecyl arsonium, phenyl arsonium, benzyl arsonium, and the like. The analogous antimony and bismuth-containing cations may also be of utility.

Examples of polypnicogen-containing cations include N,N'-bis(trimethyl)propylene diammonium, N,N'-bis(triphenyl)propylene diammonium, N,N'-bis(trioctadecyl)propylene diammonium, N,N'-diheptyl-4,4'-bipyridinium, N,N'-bis(trimethyl) ethylene diammonium, P,P'-bis(trimethyl)propylene diphosphonium, As,As'-bis(trimethyl)propylene diarsonium, 4-N,N,N',N'-tetraethyl-phenylene diammonium, and the like.

Organopnicogen-containing perrhenate compounds suitable for use in the process of this invention may be prepared using any of the methods known in the art. Such methods are described, for example, in the following publications, all of which are incorporated herein by reference in their entirety: Williams et al., *Inorg. Synth.* 26, 386(1989); Burkert et al., *Z. Naturforsch, B: Chem. Sci.* 45(6), 725(1990); Bolshakov et al., *Izv. Vyssh. Ucheb. Zaved, Khim. Tekhnol.* 15(3), 334(1972); Bondarenko et al., *Zh. Obsh. Khim.* 53, 1778(1983), Kholopova et al., *Zh. Obsh. Khim.* 53, 1285(1983), and Okrasinski et al., *J. Inorg. Nucl. Chem.* 36(8), 1908(1974). Mixtures of organopnicogen-containing perrhenate compounds may be employed as catalyst in the process of this invention if desired.

The organopnicogen-containing perrhenate catalyst may be introduced into the reaction system as a preformed compound or, in another embodiment, in precursor form convertible to the active catalyst by chemical reaction. In one preferred variation of the latter embodiment, an alkali metal perrhenate salt and a halide salt of the organopnicogen-containing cation are simultaneously employed such that an organopnicogen-containing perrhenate catalyst is generated in situ. A separate catalyst preparation step thus is not required. Other variations of this approach will be apparent to those skilled in the art wherein the perrhenate anion is introduced in the form of an ammonium, alkaline earth, or heavy metal salt and the organopnicogen-containing cation is introduced in the form of a halide, nitrate, nitrite, sulfate, sulfite, chlorate, chlorite, or carboxylate salt reactive with the perrhenate salt under the conditions employed. In this embodiment, it is preferred to use approximately equivalent (i.e., stoichiomatric) amounts of each precursor component. For example, where the alkali metal perrhenate salt is potassium perrhenate and the organopnicogen halide salt is tetra-n-butyl ammonium chloride, it is desirable that the molar ratio of the two be from about 4:1 to 1:4.

In another embodiment of this invention, the organopnicogen-containing cation may be anchored or immobilized on a solid support such that the reaction mixture during epoxidation is heterogeneous. The support may be inorganic in character such as alumina, clay, zeolite or silica gel or alternatively may be an organic polymer. The support may have the cation affixed thereto through adsorption, reaction, or graft polymerization. Such supports comprising organopnicogen-containing cations are well known and are described, for example, in the following representative publications, all of which are incorporated hereby by reference in their entirety: U.S. Pat. Nos. 4,982,021 and 4,430,496; Japanese Kokai No. 50-32085 and 52-26386; P. Tundo et al., *J. Am. Chem. Soc.* 104, 6547(1982); P. Tundo et al., *J. Am. Chem. Soc.* 104, 6551(1982); German Pat. No. 2,433,409; U.S. Pat. Nos. 4,417,066 and 4,410,669. The preparation of perrhenate-containing catalysts from such supports may be carried out using methods similar to those described for the analogous vanadium, molybdenum, and titanium-containing supported catalysts of U.S. Pat. No. 4,982,021, the teachings of which are incorporated herein by reference in their entirety.

The amount of organopnicogen-containing perrhenate used in the process of this invention is not critical, but should be sufficient to catalyze the oxidation of the olefin substrate by the organic hydroperoxide. Molar ratios of olefin:rhenium of from about 10,000:1 to 1:1 will generally be appropriate for achieving useful yields of epoxide within commercially feasible reaction times, owing to the relatively high catalytic activity of the organopnicogen-containing catalyst. Preferably, however, the olefin:rhenium molar ratio is from about 2000:1 to about 50:1.

The organic hydroperoxide to be used as the oxidizing agent in the process of this invention may be any organic compound having at least one hydroperoxy functional group (—OOH). Secondary and tertiary hydroperoxides are preferred, however, owing to the higher instability and greater safety hazards associated with primary hydroperoxides. The organic hydroperoxide preferably has the general structure

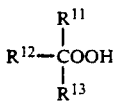

wherein $R^{11}$, $R^{12}$, and $R^{13}$ are the same or different and are selected from the group consisting of hydrogen, methyl, ethyl, and phenyl. Exemplary organic hydroperoxides include t-butyl hydroperoxide, t-amyl hydroperoxide, cumene hydroperoxide, ethyl benzene hydroperoxide, cyclohexane hydroperoxide, methyl cyclohexane hydroperoxide, tetralin hydroperoxide, isobutyl benzene hydroperoxide, isopropyl hydroperoxide, ethyl naphthalene hydroperoxide, and the like. Mixtures of organic hydroperoxides may also be employed. The amount of organic hydroperoxide is not critical, but most suitably the molar ratio of olefin:organic hydroperoxide is suitably from about 100:1 to 1:100 when the olefin contains one ethylenically unsaturated group. The molar ratio of ethylenically unsaturated groups in the olefin substrate to organic hydroperoxide is more preferably in the range of from 20:1 to 1:5. One equivalent of hydroperoxide is theoretically required to oxidize one equivalent of a mono-unsaturated olefin substrate, but it may be desirable to employ an excess of one reactant to optimize selectivity to the epoxide.

The olefin substrate may be any organic compound having at least one ethylenically unsaturated functional group (i.e., a carbon-carbon double bond) and may be an aromatic, aliphatic, mixed aromatic-aliphatic (e.g., aralkyl), cyclic, branched or straight chain olefin. Preferably, the olefin contains from 2 to 30 carbon atoms (i.e., a $C_2$-$C_{30}$ olefin). More than one carbon-carbon double bond may be present in the olefin; dienes, trienes, and other polyunsaturated substrates thus may be used. Other examples of suitable substrates include unsaturated fatty acids or fatty acid derivatives such as esters or glycerides and oligomeric or polymeric unsaturated compounds such as polybutadiene.

The olefin may contain substituents other than hydrocarbon substituents such as halide, carboxylic acid, ether, hydroxy, thiol, nitro, cyano, ketone, ester, anhydride, amino, and the like.

Exemplary olefins suitable for use in the process of this invention include ethylene, propylene, the butenes, butadiene, the pentenes, isoprene, 1-hexene, 3-hexene, 1-heptene, 1-octene, diisobutylene, 1-nonene, 1-tetradecene, pentamyrcene, camphene, 1-undecene, 1-dodecene, 1-tridecene, 1-tetradecene, 1-pentadecene, 1-hexadecene, 1-heptadecene, 1-octadecene, 1-nonadecene, 1-eicosene, the trimers and tetramers of propylene, polybutadiene, polyisoprene, cyclopentene, cyclohexene, cycloheptene, cyclooctene, cyclooctadiene, cyclododecene, cyclododecatriene, dicyclopentadiene, methylenecyclopropane, methylenecyclopentane, methylenecyclohexane, vinylcyclohexane, vinyl cyclohexene, methallyl ketone, allyl chloride, allyl bromide, acrylic acid, methacrylic acid, crotonic acid, vinyl acetic acid, crotyl chloride, methallyl chloride, the dichlorobutenes, allyl alcohol, allyl carbonate, allyl acetate, alkyl acrylates and methacrylates, diallyl maleate, diallyl phthalate, unsaturated triglycerides such as soybean oil, and unsaturated fatty acids, such as oleic acid, linolenic acid, linoleic acid, erucic acid, oleostearic acid, myristic acid, palmitic acid, and ricinoleic acid and their esters.

The process of this invention is particularly well suited for the epoxidation of olefins wherein the ethylenically unsaturated functional group of the olefin bears at least one aromatic substituent. The aromatic substituent may be phenyl, substituted phenyl such as halo phenyl, alkyl phenyl, or alkoxy phenyl, naphthyl, or substituted naphthyl, or the like. Particularly preferred are alkenyl aromatic compounds, especially those having the general structure

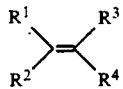

wherein at least one of $R^1$, $R^2$, $R^3$, or $R^4$ is an aromatic substituent (e.g., phenyl, naphthyl, anthryl and substituted derivatives thereof) and the remaining R substituents are selected from the group consisting of hydrogen and $C_1$-$C_8$ alkyl. Examples of alkenyl aromatic compounds include styrene, α-methyl styrene, β-methyl styrene, divinyl benzene, 1,2-dihydronaphthalene, indene, stilbene, cinnamyl alcohol, 2-methyl-1-phenyl-1-propene, 2-methyl-3-phenyl-2-propen-1-ol, cinnamyl acetate, cinnamyl bromide, cinnamyl chloride, 4-stilbenemethanol, ar-methyl styrene, ar-ethyl styrene, ar-tert-butyl styrene, ar-chlorostyrene, 1,1-diphenylethylene, vinyl benzyl chloride, vinyl naphthalene, vinyl benzoic acid, ar-acetoxy styrene, ar-hydroxy styrene (i.e., vinyl phenol), 2- or 3-methyl indene, 2,4,6-trimethylstyrene, 1-phenyl-1-cyclohexene, 1,3-diisopropenyl benzene, vinyl anthracene, vinyl anisole, and the like.

An organic solvent or mixture of organic solvents may additionally be present when the olefin is contacted with the hydroperoxide and catalyst. The solvent may be used to dilute, disperse, or dissolve the components of the reaction mixture, thus providing better temperature control or faster reaction rates. The identity of the solvent may advantageously be altered to control the rate or selectivity of the epoxidation process. Examples of suitable organic solvents include, but are not limited to, aliphatic hydrocarbons (e.g., hexane, cyclohexane, petroleum ether), aromatic hydrocarbons (e.g., benzene, toluene, xylene, ethyl benzene, naphthalene, cumene), and halogenated hydrocarbons (e.g., methylene chloride, chloroform, carbon tetrachloride, trichloroethane, chlorobenzene). The amount of organic solvent is not critical, but typically will be from about 5 to 95 weight % of the total reaction mixture. It is generally desirable to carry out the process of this invention under an inert atmosphere, that is, in the absence of oxygen.

An unexpected advantage of the process of this invention is the reduced tendency of the organopnicogen-containing perrhenate catalyst as compared to other epoxidation catalysts to be inhibited by water, alcohol, ethers, or other Lewis bases in the reaction mixture. It is well known that other transition metal epoxidation catalysts such as molybdenum coordinate strongly with Lewis bases, thereby reducing the rate of reaction. Since the organic hydroperoxide is converted to an alcohol as the epoxidation reaction proceeds, pushing the epoxidation to high conversion can consequently be difficult. This is a particular problem if a relatively high boiling epoxide is the desired product, since such epoxides are difficult to separate from a reaction mixture containing large amounts of unreacted olefin and hydroperoxide. In contrast, the use of the organopnicogen-containing perrhenate catalysts of this invention permits high yields of epoxide to be attained in a batch-type process since such catalysts are inhibited to a much lesser extent than prior art epoxidation catalysts. Thus, alcohols may be used as a reaction solvent, including those alcohols corresponding to the organic hydroperoxide component of the reaction mixture such as t-butyl alcohol, t-amyl alcohol, methyl benzyl alcohol, cumyl alcohol, cyclohexanol, methyl cyclohexanol, isopropyl alcohol, and the like.

In one embodiment of the invention, both water and a water-immiscible organic solvent are present such that a biphasic reaction mixture is formed. The water, for example, may be introduced through the use of an aqueous solution of an organic hydroperoxide such as tertiary butyl hydroperoxide as described earlier. Surprisingly, selectivity to epoxide remains high under these conditions with minimal formation of glycol by-products despite the presence of the water. This result was particularly unexpected in view of the teaching in the prior art (U.S. Pat. Nos. 4,564,715 and 4,982,021) that perrhenate compounds of the type used herein will catalyze the hydrolysis of epoxides to glycols. The olefin substrate itself and/or the organic hydroperoxide may serve as the organic solvent if sufficiently immiscible with water. Generally, the solvent will be selected such that the organopnicogen-containing perrhenate catalyst is substantially dissolved in the organic phase of the reaction mixture in preference to the aqueous phase. The organic solvents described hereinabove, especially the aliphatic hydrocarbons, aromatic hydrocarbons, halogenated aliphatic hydrocarbons, and halogenated aromatic hydrocarbons are especially preferred for use. The amount of water employed in this embodiment of the invention is not critical and typically can be varied from 1 to 75 weight % of the total reaction mixture.

The reaction temperature is not critical, but should be sufficient to accomplish substantial conversion of the olefin to epoxide within a reasonably short period of time. It is generally advantageous to carry out the reaction to achieve as high a hydroperoxide conversion as possible, preferably at least 50% and desirably at least 90%, consistent with reasonable selectivities. The optimum reaction temperature will be influenced by catalyst activity, olefin reactivity, reactant concentrations, and type of solvent employed, among other factors, but typically will be in a range of from about 0° C. to 150° C. More preferably, the temperature will be from about 20° C. to 100° C. Reaction times of from about 10 minutes to 48 hours will typically be appropriate, depending upon the above-identified variables. Although subatmospheric pressures can be employed, the reaction is preferably performed at atmospheric pressure or at elevated pressure (typically, not greater than about 2,000 psig). Generally, it will be desirable to maintain the reaction components as a liquid phase mixture.

The process of this invention may be carried out in a batch, continuous, or semi-continuous manner using any appropriate type of reaction vessel or apparatus. Known methods for conducting transition metal catalyzed epoxidations of olefins using organic hydroperoxides will generally also be suitable for use in this process. Thus, the reactants may be combined all at once or sequentially. For example, the organic hydroperoxide may be added incrementally to the reaction zone. Once the epoxidation has been carried out to the desired degree of conversion, the desired epoxide product may be separated and recovered from the reaction mixture using any appropriate technique such as fractional distillation, extractive distillation, liquid-liquid extraction, crystallization, or the like. The co-product of the reaction will generally be the corresponding alcohol derived from the organic hydroperoxide and may similarly be separated and recovered for use as a valuable product in its own right. For example, t-butyl alcohol will be produced if t-butyl hydroperoxide is employed as the oxidant while methyl benzyl alcohol is obtained using ethyl benzene hydroperoxide. The alcohol product can in turn be readily dehydrated to a useful olefin such as isobutylene or styrene. After separating from the epoxidation reaction mixture, the recovered organopnicogen-containing perrhenate catalyst may be economically re-used in subsequent epoxidations. Similarly, any unreacted olefin or organic hydroperoxide may be separated and recycled.

From the foregoing description, one skilled in the art can readily ascertain the essential characteristics of this invention, and, without departing from the spirit and scope thereof, can make various changes and modifications of the invention to adapt it to various usages, conditions, and embodiments.

The following examples further illustrate the process of this invention, but are not limitative of the invention in any manner whatsoever.

EXAMPLE 1

Tetrabutyl ammonium perrhenate [(n-Bu$_4$N)(ReO$_4$)] was prepared by adding an aqueous solution of tetrabutyl ammonium chloride (0.96 g; 3.5 mmole) to an aqueous solution of potassium perrhenate (1.0 g; 3.5 mmole in 50 g boiling water). The white precipitate of tetrabutyl ammonium perrhenate thus obtained was collected by filtration, washed several times with water, and vacuum dried.

A reaction mixture containing tetrabutyl ammonium perrhenate (0.065 g; 0.13 mmole), methylene chloride (20 g), trans-β-methyl-styrene (0.15 g; 1.3 mmole), and 3M t-butyl hydroperoxide in isooctane (0.6 g 2.6 mmole TBHP) was refluxed at 40° C. for 16 hours. Epoxide yield was followed by GC using hexadecane as internal standard. Conversion of the olefin substrate was 78% with 85% selectivity to trans-β-methylstyrene oxide; the yield of epoxide product was 65%.

EXAMPLE 2

This example illustrates the use of an aqueous solution of an organic hydroperoxide in a two-phase reaction medium in accordance with the process of this invention. A biphasic mixture containing potassium perrhenate (0.01 g), tetrabutyl ammonium chloride (0.01 g), 70% aqueous t-butyl hydroperoxide (0.5 g), trans-β-methylstyrene (0.15 g), and methylene chloride (20 g) was refluxed at 40° C. for 17 hours. Olefin conversion was 52%, while selectivity to trans-β-methylstyrene oxide was determined to be 88% with negligible formation of hydrolysis by-products.

EXAMPLE 3

This example demonstrates the use of an organophosphonium perrhenate catalyst in the process of this invention.

Potassium perrhenate (1.0 g; 3.5 mmole) was dissolved in 50 g boiling water. An aqueous solution containing tetraphenyl phosphonium chloride (1.31 g; 3.5 mmole) was added with stirring to form a white precipitate of tetraphenyl phosphonium perrhenate [(Ph$_4$P)(ReO$_4$)]. The precipitate was collected by filtration, washed several time with water, and vacuum dried.

A mixture containing the above-prepared tetraphenyl phosphonium perrhenate (0.78 g; 0.13 mmole), methylene chloride (20 g), trans-β-methylstyrene (0.15 g; 1.3 mmole), and 3M t-butyl-hydroperoxide in isooctane (0.6 g; 2.6 mmole TBHP) was refluxed at 40° C. for 16 hours. Olefin conversion was 72% with 87% selectivity to trans-β-methylstyrene oxide (63% yield).

EXAMPLES 4–11

To demonstrate the use of other organic hydroperoxides and other olefin substrates in the process of this invention, the epoxidation reactions shown in Table 1 were performed. One equivalent of olefin, two equivalents of organic hydroperoxides, 1 mole % tetrabutyl ammonium perrhenate catalyst, and methylene chloride solvent were combined and reacted as described in Example 1 using the reaction temperatures and times indicated in the table. Comparative examples 9–11 show that hydrogen peroxide cannot successfully be used as a replacement for the organic hydroperoxide in the process of this invention as little or none of the desired epoxide is formed.

TABLE I

| Ex. | Olefin | Hydroperoxide | Temp. (°C.) | Time (hr) | Epoxide | Epoxide Yield % |
|---|---|---|---|---|---|---|
| 4 | 1-octene | TBHP[1] | 40 | 18 | 1-octene oxide | <5 |
| 5 | trans-β-methylstyrene | EBHP[2] | 40 | 16 | trans-β-methylstyrene oxide | 40 |
| 6 | cyclohexene | TBHP | 40 | 16 | cyclohexene oxide | <5 |
| 7 | α-methylstyrene | TBHP | 40 | 8 | α-methylstyrene oxide | 46 |
| 8 | cis-β-methylstyrene | TBHP | 40 | 16 | trans-β-methylstyrene oxide | 45 |
| 9* | 1-octene | H$_2$O$_2$ | 25 | 62 | — | 0 |
| 10* | trans-β-methylstyrene | H$_2$O$_2$ | 25 | 62 | — | 0[3] |
| 11* | cis-β-methylstyrene | H$_2$O$_2$ | 40 | 18 | — | 0[3] |

*Comparative example
[1] t-butyl hydroperoxide
[2] ethylbenzene hydroperoxide
[3] about 20% yield of benzaldehyde was obtained

EXAMPLES 12–23

These examples illustrate the use of various organopnicogen-containing perrhenate catalysts, organic hydroperoxides, olefin substrates, and solvents in the epoxidation process of this invention. The epoxidations are performed in accordance with the procedure of Example 1 using a 2:1 molar ratio of hydroperoxide:olefin, 5 mole % (based on olefin) organopnicogen-containing perrhenate catalyst, and 75 weight percent (based on the total weight of the reaction mixture) of the solvent indicated. The epoxidations are carried out in standard laboratory glassware where the reaction temperature is less than the boiling points of the reactants and solvent and in a stainless steel autoclave where the reaction temperature is greater than the boiling point of the most volatile reaction mixture component.

TABLE II

| Ex. | Olefin | Catalyst | Hydroperoxide | Solvent | Temp (°C.) | Time (hr) | Expected Product |
|---|---|---|---|---|---|---|---|
| 12 | vinyl cyclohexane | (Me)$_4$AsReO$_4$ | TBHP[1] | t-butyl alcohol | 50 | 20 | vinyl cyclohexane oxide |
| 13 | stilbene | Et$_2$Me$_2$NReO$_4$ | TAHP[2] | t-amyl alcohol | 80 | 5 | stilbene oxide |
| 14 | allyl chloride | n-C$_{12}$H$_{25}$NH$_3$ReO$_4$ | CHP[3] | cumene | 75 | 3 | epichlorohydrin |
| 15 | indene | PhCH$_2$NMe$_3$ReO$_4$ | EBHP[4] | ethylbenzene | 100 | 10 | indiene oxide |
| 16 | allyl alcohol | (n-C$_6$H$_{13}$)$_2$NHReO$_4$ | CHHP[5] | cyclohexane | 60 | 12 | glycidol |
| 17 | methyl oleate | n-C$_6$H$_{13}$PPh$_3$ReO$_4$ | TBHP[1] | toluene | 110 | 15 | 9,10-epoxy undecanoic acid methyl ester |
| 18 | 2,3-dimethyl-2-butene | 1-hexadecylpyridinium perrhenate | TAHP[2] | dichloroethane | 45 | 8 | 2,3-dimethyl-2-butene oxide |
| 19 | propylene | iso-C$_4$H$_9$PPh$_3$ReO$_4$ | CHP[3] | chlorobenzene | 100 | 3 | propylene oxide |
| 20 | 1-butene | (n-Bu)$_4$AsReO$_4$ | EBHP[4] | benzene | 90 | 6 | 1-butene oxide |
| 21 | allyl phenyl ether | Ph$_4$AsReO$_4$ | CHHP[5] | mixed hexanes | 85 | 2 | phenyl glycidyl ether |
| 22 | isobutylene | Me$_4$SbReO$_4$ | TBHP[1] | mixed xylenes | 65 | 20 | isobutylene oxide |
| 23 | norbornene | 1-phenethyl-2-picolinium | EBHP[4] | ethyl benzene | 70 | 18 | norbornene oxide |

| Ex. | Olefin | Catalyst | Hydroperoxide | Solvent | Temp (°C.) | Time (hr) | Expected Product |
|---|---|---|---|---|---|---|---|
| | | perrhenate | | | | | |

[1] t-butyl hydroperoxide
[2] t-amyl hydroperoxide
[3] cumene hydroperoxide
[4] ethyl benzene hydroperoxide
[5] cyclohexane hydroperoxide

I claim:

1. A process for epoxidizing an olefin comprising contacting the olefin with an organic hydroperoxide in the presence of an amount of a rhenium catalyst comprised of a perrhenate anion and an organopnicogen-containing cation effective to form an epoxide of the olefin.

2. The process of claim 1 wherein the pnicogen of the organopnicogen-containing cation is N, P, or As.

3. The process of claim 1 wherein the organopnicogen-containing cation has the general formula $$RR^1R^2R^3Pn$$

wherein R, $R^1$, $R^2$ and $R^3$ are the same or different and are selected from the group consisting of hydrogen, $C_1$–$C_{20}$ linear, branched, or cyclic alkyl, $C_6$–$C_{20}$ aryl, and $C_7$–$C_{20}$ aralkyl, with the proviso that not all of R, $R^1$, $R^2$, and $R^3$ are hydrogen, and Pn is N, P, or As; or the general formula $$R^4R^5R^6Pn^2\text{--}R^7\text{--}Pn^3R^3R^9R^{10}$$

wherein $R^4$, $R^5$, $R^6$, $R^7$, $R^8$, $R^9$, $R^{10}$ are the same or different and are selected from the group consisting of hydrogen, $C_1$–$C_{20}$ linear, branched, or cyclic alkyl, $C_6$–$C_{20}$ aryl, and $C_7$–$C_{20}$ aralkyl, with the proviso that $R^7$ is not hydrogen, and $Pn^2$ and $Pn^3$ are the same or different and are N, P, or As.

4. The process of claim 1 wherein the olefin is an alkenyl aromatic compound.

5. The process of claim 1 wherein the organic hydroperoxide is a secondary or tertiary hydroperoxide having the general structure $$R^{12}\text{--}\underset{\underset{R^{13}}{|}}{\overset{\overset{R^{11}}{|}}{C}}\text{--}OOH$$

wherein $R^{11}$, $R^{12}$, and $R^{13}$ are the same or different and are selected from the group consisting of hydrogen, methyl, ethyl, and phenyl.

6. A process for epoxidizing an olefin wherein at least one of the ethylenically unsaturated functional groups of the olefin bears an aromatic substituent, said process comprising contacting the olefin with a secondary or tertiary hydroperoxide having the general structure $$R^{12}\text{--}\underset{\underset{R^{13}}{|}}{\overset{\overset{R^{11}}{|}}{C}}\text{--}OOH$$

wherein $R^{11}$, $R^{12}$, and $R^{13}$ are the same or different and are selected from the group consisting of hydrogen, methyl, ethyl, and phenyl in the presence of a rhenium catalyst having the general formula $$[RR^1R^2R^3Pn][ReO_4]$$

wherein R, $R^1$, $R^2$, and $R^3$ are the same or different and are selected from the group consisting of hydrogen, $C_1$–$C_{20}$ linear, branched, or cyclic alkyl, $C_6$–$C_{20}$ aryl, and $C_7$–$C_{20}$ aralkyl, with the proviso that not all of R, $R^1$, $R^2$, and $R^3$ are hydrogen, and Pn is N, P, or As, effective to form an epoxide of the olefin.

7. The process of claim 6 wherein the olefin has the general structure $$\underset{R^{15}}{\overset{R^{14}}{\diagdown}}C=C\underset{R^{17}}{\overset{R^{16}}{\diagup}}$$

wherein at least one of $R^{14}$, $R^{15}$, $R^{16}$, or $R^{17}$ is an aromatic substituent and the remaining R substituents are the same or different and are selected from the group consisting of hydrogen and $C_1$–$C_8$ alkyl.

8. The process of claim 6 wherein the secondary or tertiary organic hydroperoxide is selected from the group consisting of t-butyl hydroperoxide, t-amyl hydroperoxide, cumene hydroperoxide, and ethyl benzene hydroperoxide.

9. The process of claim 6 wherein none of R, $R^1$, $R^2$, or $R^3$ is hydrogen.

10. The process of claim 6 wherein the molar ratio of olefin:organic hydroperoxide is from about 100:1 to 1:100.

11. The process of claim 6 wherein the molar ratio of olefin:rhenium is from about 10,000:1 to 1:1.

12. The process of claim 6, wherein said contacting is carried out at a temperature of from about 0° C. to 150° C.

13. The process of claim 6 wherein said contacting is carried out for a time of from about 10 minutes to 48 hours.

14. The process of claim 6 wherein an organic solvent is additionally present during said contacting.

15. A process for epoxidizing an olefin comprising contacting the olefin with an organic hydroperoxide in the presence of catalytically effective amounts of an alkali metal perrhenate and an organopnicogen halide salt.

16. The process of claim 15 wherein the alkali metal perrhenate is lithium perrhenate, sodium perrhenate, or potassium perrhenate.

17. The process of claim 15 wherein the organopnicogen halide salt has the general formula $$RR^1R^2R^3PnX$$

wherein R, $R^1$, $R^2$, and $R^3$ are the same or different and are selected from the group consisting of hydrogen, $C_1$–$C_{20}$ linear, branched, or cyclic alkyl, $C_6$–$C_{20}$ aryl, and $C_7$–$C_{20}$ aralkyl, with the proviso that not all of R, $R^1$, $R^2$, and $R^3$ are hydrogen, Pn is N, P, or As, and X is Cl, Br, or I; or the general formula $$X^2R^4R^5R^6Pn^2-R^7-Pn^3R^8R^9R^{10}X^3$$

wherein $R^4$, $R^5$, $R^6$, $R^7$, $R^8$, $R^9$, and $R^{10}$ are the same or different and are selected from the group consisting of hydrogen, $C_1$–$C_{20}$ linear, branched, or cyclic alkyl, $C_6$–$C_{20}$ aryl, and $C_7$–$C_{20}$ aralkyl, with the proviso that $R^7$ is not hydrogen, $Pn^2$ and $Pn^3$ are the same or different and are N, P, or As, and $X^2$ and $X^3$ are the same or different and are N, P, or As.

18. The process of claim 15 wherein an organic solvent is additionally present.

19. The process of claim 15 wherein water is additionally present.

20. The process of claim 15 wherein both water and an organic solvent are additionally present.

21. The process of claim 15 wherein the organic hydroperoxide is a secondary or tertiary hydroperoxide having the general structure

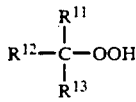

wherein $R^{11}$, $R^{12}$, and $R^{13}$ are the same or different and are selected from the group consisting of hydrogen, methyl, ethyl, and phenyl.

22. The process of claim 15 wherein the olefin is an alkenyl aromatic compound.

23. A process for epoxidizing an olefin wherein at least one of the ethylenically unsaturated functional groups of the olefin bears an aromatic substituent, said process comprising contacting a secondary or tertiary hydroperoxide having the general structure

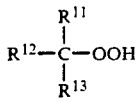

wherein $R^{11}$, $R^{12}$, and $R^{13}$ are the same or different and are selected from the group consisting of hydrogen, methyl, ethyl, and phenyl with the olefin in a biphasic reaction mixture containing water, a water-immiscible organic solvent, and catalytically effective amounts of an alkali metal perrhenate and an organopnicogen halide salt.

24. The process of claim 23 wherein the alkali metal perrhenate is lithium perrhenate, sodium perrhenate, or potassium perrhenate.

25. The process of claim 23 wherein the organopnicogen halide salt has the general formula $$RR^1R^2R^3PnX$$

wherein R, $R^1$, $R^2$, and $R^3$ are the same or different and are selected from the group consisting of hydrogen, $C_1$–$C_{20}$ linear, branched, or cyclic alkyl, $C_6$–$C_{20}$ aryl, and $C_7$–$C_{20}$ aralkyl, with the proviso that not all of R, $R^1$, $R^2$, and $R^3$ are hydrogen, Pn is N, P, or As, and X is Cl, Br, or I; or the general formula $$X^2R^4R^5R^6Pn^2-R^7-Pn^3R^8R^9R^{10}X^3$$

wherein $R^4$, $R^5$, $R^6$, $R^7$, $R^8$, $R^9$, and $R^{10}$ are the same or different and are selected from the group consisting of hydrogen, $C_1$–$C_{20}$ linear, branched, or cyclic alkyl, $C_6$–$C_{20}$ aryl, and $C_7$–$C_{20}$ aralkyl, with the proviso that $R^7$ is not hydrogen, $Pn^2$ and $Pn^3$ are the same or different and are N, P, or As, and $X^2$ and $X^3$ are the same or different and are N, P, or As.

26. The process of claim 23 wherein the water-immiscible organic solvent is selected from the group consisting of halogenated aliphatic hydrogens, halogenated aromatic hydrocarbons, aliphatic hydrocarbons, and aromatic hydrocarbons.

27. The process of claim 23 wherein the olefin has the general structure

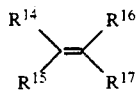

wherein at least one of $R^{14}$, $R^{15}$, $R^{16}$, or $R^{17}$ is an aromatic substituent and the remaining R substituents are selected from the group consisting of hydrogen and $C_1$–$C_8$ alkyl.

28. The process of claim 23 wherein $R^{11}$, $R^{12}$, $R^{13}$ are each methyl.

29. The process of claim 23 wherein the molar ratio of alkali metal perrhenate:organopnicogen halide salt is from 4:1 to 1:4.

* * * * *